United States Patent [19]

Shirahase et al.

[11] Patent Number: 5,122,455
[45] Date of Patent: Jun. 16, 1992

[54] GOT ISOZYME ASSAY

[75] Inventors: Yasushi Shirahase, Kobe; Yoshifumi Watazu, Akashi, both of Japan

[73] Assignees: International Reagents Corporation, Hyogo; Amano Pharmaceutical Co., Ltd., Aichi, both of Japan

[21] Appl. No.: 483,747

[22] Filed: Feb. 23, 1990

[30] Foreign Application Priority Data

Mar. 3, 1989 [JP] Japan .................... 1-52687

[51] Int. Cl.⁵ .................... C12Q 1/48; C12Q 1/52; C12N 9/99
[52] U.S. Cl. ........................ 435/16; 435/15; 435/23; 435/184; 435/183
[58] Field of Search .............. 435/16, 23, 187

[56] References Cited

U.S. PATENT DOCUMENTS 4,702,909 10/1987 Villajeros et al. .............. 424/89
4,769,323 9/1988 Murao et al. .................. 435/16

FOREIGN PATENT DOCUMENTS 0306167 3/1989 European Pat. Off. .
6323797 10/1988 Japan ........................ 435/16

OTHER PUBLICATIONS

Gross-Ballard, M., et al. *Eur. J. Biochem.* 36:32-38, 1973.
Jany, K.-D., and Mayer, B. *Biol. Chem. Hoppe-Seyler* 366:485-492, May 1985.
Ebeling, W. et al., *Eur. J. Biochem.* 47, 91-97 (1974).
Panteghini, M. et al., *J. Clin. Chem. Clin. Biochem*, 22, 153-158 (1984).
Panteghini, M., et al. *Clinical Chemistry* 33, 67-71 (1987).
Lebherz, H. G., et al. Biological Abstracts vol. 81, No. 11, 1986, Abstract No. 101161.
Teranishi, H., et al, Clinical Biochemistry, vol. 21, 347-358 (1988).
Aoyagi, T., et al, Chemical Abstracts, vol. 85, No. 1, p. 145, 85:1676s, Jul. 1976.

*Primary Examiner*—Esther L. Kepplinger
*Assistant Examiner*—Toni R. Scheiner

[57] ABSTRACT

A glutamic-oxaloacetic transaminase (GOT) isozyme assay, which comprises selectively inhibiting s-GOT in a sample such as serum or plasma by proteinase K, optionally an excess amount of proteinase K by a protease inhibitor and then determining m-GOT remaining intact, is described.

5 Claims, No Drawings

GOT ISOZYME ASSAY

BACKGROUND OF THE INVENTION

1. Field of the Invention

The present invention relates to a GOT isozyme assay especially for clinical use.

2. DESCRIPTION OF THE RELATED ART

GOT (glutamic-oxaloacetic transaminase) is an enzyme which is contained principally in tissues such as myocardia, hepatocytes and skeletal muscles. Clinically, when such a tissue is damaged under a condition of, for example, myocardial infarction, hepatopathy, myositis and muscular dystrophy, GOT escapes into blood and therefore a GOT level is elevated in serum.

It is known that GOT has two isozymes which are separately distributed in a cell. That is, one of them is found in a supernatant fraction of the cell (s-GOT) and the other contained in a mitochondrial fraction (m-GOT). The m-GOT concentration or the m-GOT level based on the total GOT in blood is useful for diagnosis and prognosis of said diseases, in particular acute or fulminant hepatitis and alcoholic hepatitis.

Conventional GOT isozyme assay method include, for example, electrophoresis, ion-exchange assay and immunoassay methods. However, these assays are attended with complicated procedure, require long operation time and cannot be carried out with using a conventional autoanalyzer which is clinically used.

For the purpose of solving such problems, Japanese Patent Kokai Publication No. 237797/1988 discloses an isozyme assay which comprises selectively inhibiting an isozyme in a sample by a protease in the presence of a protein and determining another isozyme remaining intact.

SUMMARY OF THE INVENTION

An object of the present invention is to provide an improved GOT isozyme assay which can be carried out using the conventional autoanalyzer.

It has been found that, when proteinase K is used as the protease in the prior isozyme assay, it is possible not only to selectively inhibit s-GOT in the absence of the protein but also to stabilize the assay medium.

Accordingly, the present invention provides a GOT isozyme assay, which comprises selectively inhibiting s-GOT in a sample by proteinase K and determining m-GOT remaining intact.

DETAILED DESCRIPTION OF THE INVENTION

Proteinase K (EC 3.4.21.14), which is a serine-proteinase produced by a microorganism, in particular *Tritirachium album*, is stable in a pH range of from 6.0 to 11.0.

According to the present invention, proteinase K is usually used in an amount of from 1 to 1000 units/ml, preferably from 5 to 500 units/ml for the inhibition of s-GOT in the sample.

After the inhibition of s-GOT, m-GOT can be determined by means of a conventional enzyme assay.

In the present assay, proteinase K which is stable under an alkaline condition is used. Therefore, stable determination of m-GOT can be achieved in an alkaline medium containing, for example, NADH without deteriorating the sample and reagents.

If an excess amount of proteinase K is inactivated by a protease inhibitor after the inhibition of s-GOT, possible interference caused by the protease can be prevented in the following determination step.

Accordingly, the present invention also provides a GOT isozyme assay, which comprises selectively inhibiting s-GOT in a sample by proteinase K, inactivating an excess amount of proteinase K by a protease inhibitor and determining m-GOT remaining intact.

Specific examples of the protease inhibitor are as follows: chymostatin, aprotinin, trypsin inhibitor, leupeptin, phenylmethylsulfonyl fluoride, (p-amidinophenyl)methanesulfonyl fluoride hydrochloride and ethyl 4-(6-guanidino hexanoyloxy)benzoate methanesulfonate.

The amount of the protease inhibitor may vary with the individual determination condition. For example, when chymostatin is used as the inhibitor, its concentration is usually in the range between 0.5 and 50 mM, preferably 1 and 10 mM.

The protease inhibitor may be partly or completely incorporated in the determination reagent.

The sample to be subjected to the present assay may be a clinical sample such as serum and plasma.

PREFERRED EMBODIMENTS OF THE INVENTION

The present invention is illustrated more in detail by the following Examples.

EXAMPLE 1

To each of ten serum samples (each 0.02 ml), 40 mM CHES [2-(cyclohexylamino)ethanesulfonic acid]buffer (pH 9.0; 0.25 ml) containing NADH (0.3 mM) and proteinase K (16 units/ml) was added and reacted for 5 minutes a 37° C. Then, an enzyme assay reagent (0.1 ml) was added to the mixture at 37° C. The enzyme assay reagent consisted of 100 mM HEPES (N-2-hydroxyethylpiperazine-N'-ethanesulfonic acid) buffer (pH 7.5) containing lactate dehydrogenase (LDH; EC 1.1.1.28; 10 units/ml), malate dehydrogenase (MDH; EC 1.1.1.37; 5 units/ml), L-aspartic acid (740 mM) and α-ketoglutaric acid (45 mM). After 2 minutes, the decrease of absorbance at 340 nm was determined. Based on the data, mGOT activity was calculated.

On the other hand, the same samples were subjected to a conventional immunoassay with using an m-GOT assay kit manufactured by Eiken Chemical Co. Ltd.

The results of the present assay highly correlated to those of the conventional immunoassay as shown in Table 1.

TABLE 1

| Sample No. | m-GOT Activity (units/l) | |
|---|---|---|
| | Present assay | Prior immunoassay |
| 1 | 7 | 6 |
| 2 | 4 | 3 |
| 3 | 13 | 14 |
| 4 | 48 | 47 |
| 5 | 7 | 8 |
| 6 | 63 | 65 |
| 7 | 31 | 29 |
| 8 | 21 | 21 |
| 9 | 5 | 6 |
| 10 | 11 | 13 |

EXAMPLE 2

Proteinase K (30 units/ml) and α-chymotrypsin (EC 3.4.21.1; 500 units/ml) were each dissolved in 100 mM CHES buffer (pH 9.0), incubated at 37° C. for 2 hours and diluted (×100) with 100 mM CHES buffer (pH 9.0). To the diluted solution (0.6 ml), standard s-GOT (0.1 ml) containing one unit/ml of s-GOT was added and incubated at 37° C. for 5 minutes so that s-GOT might be inhibited. Then, after the addition of 100 mM Tris buffer (pH 7.5; 3.0 ml) containing NADH (0.2 mM), LDH (10 units/ml), L-aspartic acid (270 mM) and α-ketoglutaric acid (12 mM), remaining s-GOT activity in the solution was determined. From a calibration curve, remaining protease activity could be known.

It was found that proteinase K remained 100 % active even after the above-mentioned procedure while the activity of α-chymotrypsin was lowered to only 19 %. Thus, proteinase K is highly stable under an alkaline condition.

EXAMPLE 3

The present assay comprising the inactivation of the excess of proteinase K by the protease inhibitor was compared with the conventional immunoassay.

The following four reagents were prepared:

Reagent 1: 50 mM Tris buffer (pH 7.8) containing proteinase K (200 units/ml);

Reagent 2: 100 mM HEPES buffer (pH 7.0) containing chymostatin (5 mM), pyruvate oxidase (POP; EC 1.2.3.3; 40 units/ml), peroxidase (POD; EC 1.11.1.7; 10 units/ml), N-ethyl-N-(2-hydroxy-3-sulfopropyl)-m-toluidine (EHSPT; 2 mM), magnesium chloride (6 mM), thiamine pyrophosphate (8 mM) and potassium dihydrogen phosphate (2 mM);

Reagent 3: 100 mM HEPES buffer (pH 7.0) containing L-aspartic acid (400 mM), α-ketoglutaric acid (20 mM), 4-aminoantipyrine (0.4 mM) and oxalacetate decarboxylase (OAC; EC 4.1.1.3; 40 units/ml); and Reagent 4: 100 mM citrate buffer.

To each of ten serum samples (each 0.05 ml), the reagent 1 (50 μl) was added and incubated at 37° C. for about 5 minutes. Then, the reagent 2 (0.5 ml) was added and incubated again at 37° C. for about 5 minutes. After the addition of the reagent 3 (0.5 ml), incubation was continued exactly for 30 minutes at the same temperature. Finally, the reagent 4 (2.0 ml) was added. After about 5 minutes at a room temperature, the sample was subjected to the determination of absorbance at 555 nm. m-GOT Activities of the samples could be known from a calibration curve.

On the other hand, the same samples were subjected to a conventional immunoassay with using an m-GOT assay kit manufactured by Eiken Chemical Co. Ltd.

The results of the present assay highly correlated to those of the conventional immunoassay as shown in Table 2.

TABLE 2

| Sample No. | m-GOT Activity (units/l) | |
|---|---|---|
| | Present assay | Prior immunoassay |
| 1 | 3 | 4 |
| 2 | 5 | 6 |
| 3 | 37 | 36 |
| 4 | 9 | 11 |
| 5 | 21 | 23 |
| 6 | 6 | 5 |
| 7 | 64 | 66 |
| 8 | 4 | 3 |
| 9 | 13 | 12 |
| 10 | 16 | 18 |

What is claimed is:

1. A method for the determination of mitochondrial-fraction glutamic-oxaloacetic transaminase activity in a sample, wherein the method comprises:
   (a) contacting the sample, in the absence of other added protein, with proteinase K in an amount sufficient to inhibit supernatant-fraction glutamic-oxaloacetic transaminase, to form a first reaction mixture, and
   (b) contacting the first reaction mixture with a determination reagent to form a second reaction mixture, and determining the mitochondrial glutamic-oxaloacetic transaminase activity remaining in the second reaction mixture.

2. The method of claim 1, wherein the sample is serum or plasma.

3. The method of claim 1, wherein said determination reagent comprises lactate dehydrogenase and malate dehydrogenase, and wherein the mitochondrial glutamic-oxaloacetic transaminase activity remaining in the second reaction mixture is determined by absorption analysis.

4. The method of claim 1, wherein step (a) further comprises inactivating excess proteinase K by adding a protease inhibitor to the the first reaction mixture after the inhibition of supernatant-fraction glutamic-oxaloacetic transaminase by proteinase K.

5. The method of claim 4, wherein the protease inhibitor is selected from the group consisting of chymostatin, aprotinin, trypsin inhibitor, leupeptin, phenylmethylsulfonyl fluoride, (p-amidinophenyl) methanesulfonylfluoride hydrochloride and ethyl 4-(6-guanidino hexanoyloxy)benzoate methanesulfonate.

* * * * *